US006855856B2

(12) United States Patent
van Broekhoven et al.

(10) Patent No.: US 6,855,856 B2
(45) Date of Patent: Feb. 15, 2005

(54) PROCESS FOR THE ALKYLATION OF HYDROCARBONS

(75) Inventors: Emanuel Hermanus van Broekhoven, Monnickendam (NL); Francisco René Mas Cabré, Amstelveen (NL)

(73) Assignee: Akzo Nobel NV (NL)

( * ) Notice: Subject to any disclaimer, the term of this patent is extended or adjusted under 35 U.S.C. 154(b) by 162 days.

(21) Appl. No.: 10/395,622

(22) Filed: Mar. 24, 2003

(65) Prior Publication Data

US 2003/0181779 A1 Sep. 25, 2003

Related U.S. Application Data

(62) Division of application No. 09/863,624, filed on May 23, 2001, now abandoned.
(60) Provisional application No. 60/216,068, filed on Jul. 5, 2000.

(30) Foreign Application Priority Data

May 30, 2000 (EP) .............................................. 00201917

(51) Int. Cl.[7] ............................... C07C 2/56; C07C 2/58
(52) U.S. Cl. ........................ 585/722; 585/721; 585/709
(58) Field of Search ................................ 585/709, 721, 585/722

(56) References Cited

U.S. PATENT DOCUMENTS

| | | | | |
|---|---|---|---|---|
| 4,008,291 A | * | 2/1977 | Zabransky et al. .......... | 585/720 |
| 4,185,040 A | * | 1/1980 | Ward et al. ................... | 502/64 |
| 4,442,223 A | * | 4/1984 | Chester et al. ................ | 502/68 |
| 4,683,052 A | * | 7/1987 | Degnan et al. ......... | 208/111.35 |
| 5,118,896 A | * | 6/1992 | Steigelmann et al. ....... | 585/467 |
| 5,243,116 A | * | 9/1993 | Lee et al. .................... | 585/467 |
| 5,292,426 A | * | 3/1994 | Holland et al. ......... | 208/111.25 |
| 5,384,297 A | * | 1/1995 | Prada et al. .................. | 502/66 |
| 5,393,408 A | * | 2/1995 | Ziemer et al. ................ | 208/57 |
| 5,393,409 A | * | 2/1995 | Jan et al. ..................... | 208/108 |
| 5,523,503 A | * | 6/1996 | Funk et al. .................. | 585/446 |
| 5,543,035 A | * | 8/1996 | Ziemer ..................... | 208/111.3 |
| 5,620,590 A | * | 4/1997 | Absil et al. .............. | 208/111.3 |
| 5,986,158 A | * | 11/1999 | Van Broekhoven et al. | 585/722 |
| 2003/0092948 A1 | * | 5/2003 | van Broekhoven et al. . | 585/446 |

FOREIGN PATENT DOCUMENTS

| | | | | |
|---|---|---|---|---|
| DE | 23 54 558 A1 | 5/1975 | ............ | B01J/35/10 |
| EP | 0 216 938 A1 | 4/1987 | ............ | B01J/29/16 |
| EP | 0 389 041 A1 | 9/1990 | | |
| EP | 0 216 938 B1 | 12/1990 | ............ | B01J/29/16 |
| EP | 0 389 041 B1 | 10/1993 | ............ | B10J/21/06 |
| EP | 0 389 041 B2 | 10/1993 | ............ | B10J/21/06 |
| EP | 0 389 041 B2 | 12/1997 | ............ | B01J/21/06 |
| WO | WO 98/23560 | 6/1998 | ............ | C07C/2/58 |
| WO | WO 98/42805 | 10/1998 | ........... | C10G/47/18 |

* cited by examiner

*Primary Examiner*—Christina Johnson
(74) *Attorney, Agent, or Firm*—Louis A. Morris

(57) ABSTRACT

The invention pertains to a process for the alkylation of hydrocarbons wherein a hydrocarbon feedstock and an olefin are contacted with a catalyst at alkylation process conditions. The catalyst comprises a hydrogenation function and a solid acid. The ratio between (i) the volume in catalyst pores with a diameter in the range of about 40–8000 nm and (ii) the specific length of the catalyst particles is in the range of about 0.01–0.90 ml/(g*mm). The catalyst has a total pore volume of at least about 0.20 ml/g and the volume in the catalyst pores with a diameter in the range of about 40–8000 nm is below about 0.30 ml/g.

11 Claims, No Drawings

PROCESS FOR THE ALKYLATION OF HYDROCARBONS

CROSS REFERENCE TO RELATED APPLICATIONS

This application is a division of U.S. application Ser. No. 09/863,624, filed May 23, 2001 now abandoned, which claims priority from European Application No. 00201917, filed May 30, 2000 and from U.S. Application Ser. No. 60/216,068, filed Jul. 5, 2000.

BACKGROUND OF THE INVENTION

1. Field of the Invention

The present invention relates to a novel process for the alkylation of hydrocarbons.

2. Description of the Prior Art

Within the framework of the present invention, the term alkylation refers to the reaction of a hydrocarbon, such as an aromatic or a saturated hydrocarbon, with an olefin. Without limiting the scope of the invention we will further illustrate the invention by discussing the alkylation of saturated hydrocarbons, in general branched saturated hydrocarbons, with an olefin to give highly branched saturated hydrocarbons with a higher molecular weight. This reaction is of interest because it makes it possible to obtain, through the alkylation of isobutane with an olefin containing 2–6 carbon atoms, an alkylate which has a high octane number and which boils in the gasoline range.

Unlike gasoline obtained by cracking heavier petroleum fractions such as vacuum gas oil and atmospheric residue, gasoline obtained by alkylation is essentially free of contaminants such as sulfur and nitrogen and so has clean burning characteristics. Its high anti-knock properties, represented by the high octane number, lessen the need to add environmentally harmful anti-knock compounds such as lead. Also, unlike gasoline obtained by reforming naphtha or by cracking heavier petroleum fractions, alkylate contains few if any aromatics or olefins, which, environmentally speaking, is a further advantage.

The alkylation reaction is acid-catalyzed. At present, in commercial alkylation equipment use is made of liquid acid catalysts such as sulfuric acid and hydrogen fluoride. The use of such catalysts is attended with a wide range of problems. For instance, sulfuric acid and hydrogen fluoride are highly corrosive, so that the equipment used has to meet high quality requirements. Since the presence of highly corrosive materials in the resulting fuel is objectionable, the remaining acid has to be removed from the alkylate. Also, because of the phase separations, which have to be carried out, the process is complicated and thus expensive. Besides, there is always the risk that toxic substances such as hydrogen fluoride will be emitted.

A newer development in this field is the use of solid acid catalysts, such as zeolite-containing catalysts. Thus WO 9823560 describes the use of a catalyst containing a zeolite, such as a Y zeolite, and a hydrogenation function, such as a Group VIII noble metal, e.g., platinum or palladium, and, optionally, a matrix material, such as alumina, in the alkylation of saturated hydrocarbons. Though the performance of this catalyst is satisfactory, there is still a need for further increase of catalytic activity, selectivity, and stability of these catalysts.

We have made a surprising discovery that satisfies the above need by choice of catalyst features as set forth in the following discussion.

SUMMARY OF THE INVENTION

Accordingly, our invention, in one embodiment, comprises a process for the alkylation of hydrocarbons wherein a hydrocarbon feedstock and an olefin are contacted with a catalyst at alkylation process conditions. The catalyst comprises a hydrogenation function and a solid acid. The ratio between (i) the volume in catalyst pores with a diameter in the range of about 40–8000 nm and (ii) the specific length of the catalyst particles is in the range of about 0.01–0.90 ml/(g*mm). The catalyst has a total pore volume of at least about 0.20 ml/g and the volume in the catalyst pores with a diameter in the range of about 40–8000 nm is below about 0.30 ml/g.

Other objectives and embodiments of our invention encompass details about catalyst compositions and physical structure, details concerning the preparation of the catalyst and the use of the catalyst all of which are hereinafter disclosed in the following discussion of each of the facets of the present invention.

DETAILED DESCRIPTION OF THE INVENTION

In the following discussion the pores having a diameter in the range of about 40–8000 nm will be denoted "macropores" and the pore volume in these pores will be designated as "macropore volume".

The specific length of the catalyst particle is defined as the ratio between the geometric volume and the geometric surface of the solid part of this catalyst particle. The determination of the geometric volume and the geometric surface is known to the person skilled in the art and can be carried out, e.g., as described in DE 2354558. It is noted that the specific length is different from the diameter of the catalyst particle. E.g., for a cylindrical catalyst particle the particle diameter is four to six times higher (depending on the diameter and the length of the particle) than the specific length. Further, the diameter of, e.g., a sphere is six times higher than the specific length.

As stated above, it is essential to the catalyst of the present invention that it has a ratio between macropore volume and specific length in the range of about 0.01–0.90 ml/(g*mm). As further stated above, it is essential to the catalyst of the present invention that it has a total pore volume of at least about 0.20 ml/g and that the macropore volume is below about 0.30 ml/g As is shown in the (comparative) examples below, the catalyst shows a significantly poorer performance in the alkylation of hydrocarbon feeds if the ratio between macropore volume and specific length and/or the total pore volume is outside these ranges.

Preferably, the ratio between macropore volume and specific length is above about 0.20 ml/(g*mm), more preferably above about 0.30 ml/(g*mm), and even more preferably above about 0.40 ml/(g*mm), as well as preferably below about 0.80 ml/(g*mm). It is further preferred that the catalyst has a total pore volume of at least about 0.23 ml/g and most preferably of at least about 0.25 ml/g.

Preferably, the catalyst particles have a specific length of at least about 0.10 mm, more preferably of at least about 0.16 mm, and most preferably of at least about 0.20 mm. The upper limit of the specific length preferably lies at about 2.0 mm, more preferably at about 1.0 mm, and most preferably at about 0.6 mm.

The particles of the catalyst of the invention can have many different shapes, including spheres, cylinders, rings, and symmetric or asymmetric polylobes, for instance tri- and quadrulobes. Preferably, the catalyst particles have an average particle diameter of at least about 0.5 mm, more preferably of at least about 0.8 mm, and most preferably of at least about 1.0 mm. The upper limit of the average particle diameter preferably lies at about 10.0 mm, more preferably at about 5.0 mm, even more preferably at about 3.0 mm.

Preferably, the macropore volume ranges from about 0.05 to about 0.30 ml/g, more preferably from about 0.08 to about 0.30 ml/g, and even more preferably from about 0.08 to about 0.25 ml/g.

The catalyst comprises a solid acid, such as a zeolite. Examples of zeolites contained in the catalyst of the invention are Y-zeolites, including H-Y-zeolites and USY-zeolites, zeolite beta, MCM-22, and MCM-36. Preferably, the zeolite is Y-zeolite with a unit cell size in the range of about 24.34–24.72 angstroms. More preferably, the zeolite is a Y-zeolite with a unit cell size in the range of about 24.40–24.61 angstroms and a silica:alumina molar ratio in the range about 7–18 and most preferably the zeolite is a Y-zeolite with a unit cell size in the range of about 24.24–24.58 angstroms and a silica:alumina molar ratio in the range about 7.85–13.75.

As stated above, the catalyst comprises a hydrogenation function. A suitable hydrogenation function, e.g., comprises a Group VIII noble metal. The Group VIII noble metal preferably is contained in the catalyst in an amount of about 0.01–2 wt %, and more preferably about 0.1–1 wt %, calculated as metal and based on the weight of the solid acid. Preferably, the Group VIII noble metal comprises palladium and/or platinum.

Preferably, the catalyst additionally comprises a matrix material. Examples of suitable matrix materials are alumina, silica, titania, zirconia, clays, and mixtures thereof. Matrix materials comprising alumina are generally preferred.

Preferably, the catalyst of the invention comprises about 2–98 wt % of the solid acid and about 98–2 wt % of the matrix material, based on the total weight of the solid acid and matrix material present in the catalyst. More preferably, the catalyst comprises about 10–90 wt % of the solid acid and about 90–10 wt % of the matrix material, based on the total weight of the solid acid and matrix material contained in the catalyst. Even more preferably, the catalyst comprises about 20–80 wt % of the solid acid and about 80–20 wt % of the matrix material, most preferably about 50–80 wt % of the solid acid and about 20–50 wt % of the matrix material, based on the total weight of the solid acid and matrix material contained in the catalyst.

If desired, the solid acid can also comprise non-zeolitic solid acids such as silica-alumina, sulfated oxides, such as sulfated oxides of zirconium, titanium, or tin, mixed oxides of zirconium, molybdenum, tungsten, phosphorus, etc., chlorinated aluminum oxides or clays.

Preferably, the catalyst consists essentially of a hydrogenation function, a solid acid, and, optionally, a matrix material. More preferably, the catalyst consists essentially of a zeolite, a Group VIII noble metal, and a matrix material. It is further preferred that the catalyst is essentially free of rare earth metals and/or Group VIII non-noble metals. Thus, most preferably, the catalyst of the invention consists essentially of a Group VIII noble metal compound, a zeolite, and a matrix, wherein (i) the zeolite consists essentially of oxidic compounds (oxides and hydroxides) of a Group III element, such as aluminum, and/or of a Group IV element, such as silicon, and, optionally, oxidic compounds of a Group I element, such as sodium, and/or of a Group II element, such as calcium, and/or of a Group V element, such as phosphorus, and, optionally, additionally ammonium and/or water, and (ii) the matrix is selected from the group of oxidic compounds of silicon, aluminum, titanium, zirconium, Group II metals or mixtures thereof.

The catalyst can be prepared by processes common to the industry. A typical process comprises the successive steps of (i) shaping, e.g., extruding the solid acid constituent, optionally after mixing it with a matrix material, to form particles, (ii) calcining the resulting particles, and (iii) incorporating the hydrogenation function into the calcined particles by, e.g., impregnating the particles with a solution of a hydrogenation metal component and/or by (competitive) ion exchange.

Alternatively, the catalyst can, e.g., be prepared by a process comprising the successive steps of (i) incorporating the hydrogenation function into the solid acid constituent or into a mixture of the solid acid constituent and the matrix material, (ii) shaping, e.g., extruding the resulting material to form particles, and (iii) calcining the resulting particles.

The catalyst is particularly suitable for the alkylation of saturated hydrocarbons. The invention therefore further pertains to the use of the catalyst of the invention in the alkylation of these feedstocks. As stated above, this comprises the reaction of a saturated hydrocarbon with an olefin or olefin precursor in the presence of the catalyst of the invention to give highly branched saturated hydrocarbons with a higher molecular weight.

Preferably, the hydrocarbon is a branched saturated hydrocarbon such as an isoalkane having about 4–10 carbon atoms. Examples are isobutane, isopentane, isohexane or mixtures thereof, with isobutane being most preferred. The olefins to be used in the alkylation process generally have about 2–10 carbon atoms, preferably 2–6 carbon atoms, still more preferably about 3–5 carbon atoms, and most preferably about 4 carbon atoms. Most preferably, the alkylation process consists of the alkylation of isobutane with butenes.

As will be evident to the skilled person, the alkylation process can be applied in any suitable form, including fluidized bed processes, slurry processes, and fixed bed processes. The process may be carried out in a number of beds and/or reactors, each with separate olefin addition. In such a case, the process of the invention may be carried out in each separate bed or reactor.

Suitable process conditions are known to the skilled person. Preferably, an alkylation process as disclosed in WO 9823560 is applied. The process conditions applied in this process are summarized in the following Table:

|  | Temperature range [° C.] | pressure range [bar] | molar ratio of saturated hydrocarbon to olefin |
|---|---|---|---|
| preferred | −40–250 | 1–100 | 5:1–5000:1 |
| more preferred | 0–150 | 10–40 | 50:1–1000:1 |
| most preferred | 60–95 | 15–30 | 150:1–750:1 |

Preferably, a regeneration technique as described in WO 9823560 is applied during the alkylation process. More in particular, during the alkylation process the catalyst is preferably subjected intermittently to a regeneration step by being contacted with a feed containing an aliphatic compound and hydrogen, with said regeneration preferably being carried out at about 90% or less, more preferably at about 60% or less, even more preferably at about 20% or less, and most preferably at about 10% or less of the active cycle of the catalyst. The active cycle of the catalyst is defined as the time from the start of the feeding of the alkylation agent to the moment when, in comparison with the entrance of the catalyst-containing reactor section, about 20% of the alkylation agent leaves the catalyst-containing reactor section without being converted, not counting isomerisation inside the molecule.

Optionally, in this process, the catalyst can be subjected periodically to a high-temperature regeneration with hydrogen in the gas phase. This high-temperature regeneration is preferably carried out at a temperature of at least about 150° C., more preferably at about 175°–600° C., and most preferably at about 200°–400° C. For details of this regeneration procedure, reference is made to WO 9823560, and in particular to page 4, lines 5–19 and page 9, line 13 through page 13, line 2.

The use of the catalyst of the present invention in the above alkylation process results in a high olefin conversion (amount of olefin in the feed that is converted in the reaction), a high C5+ alkylate yield (weight amount of C5+ alkylate produced divided by the overall weight of olefin consumed) and a high octane number, while the amount of undesired C9+ by-products can be restricted and the catalyst's stability can thus be improved. For details in respect of these parameters, reference is made to WO 9823560.

The following characterization method was applied in the present invention:

The macropore volume as well as the total pore volume were determined via mercury intrusion on the basis of the Washburn equation $$D = \frac{-4\gamma \cos\theta}{p}$$

with D being the pore diameter, p being the pressure applied during the measurement, $\gamma$ being the surface tension, taken to be 480 dynes/cm, and $\theta$ being the contact angle, taken to be 140°. In the present measurement, the pressure was varied over such a range that the measurement covered pores with a diameter in the range of 3.6–8000 nm.

The present invention will be further illustrated by way of the following examples:

General Test Procedure

A fixed-bed recycle reactor as described in WO 9823560 having a diameter of 2 cm was filled with a 1:1 volume/volume mixture of 38.6 grams of catalyst extrudates and carborundum particles (60 mesh). At the center of the reactor tube a thermocouple of 6 mm in diameter was arranged. The reactor was flushed with nitrogen for 30 minutes (100 Nl/hour). Next, the system was tested for leakages at elevated pressure, after which the pressure was raised to 21 bar and the nitrogen replaced by hydrogen (100 Nl/hour). The reactor temperature was then raised to 200° C. at a rate of 1° C./min. After 1 hour at 200° C. the temperature was raised to 400° C. at a rate of 1° C./min. After 1 hour at 400° C. the reactor temperature was lowered to the reaction temperature, which is given in the Examples below.

The hydrogen stream was stopped with the attaining of the reaction temperature. Isobutane was supplied to the reactor at a rate of about 4,000 grams/hour. About 95–98% of the isobutane was fed back to the reactor. About 2–5% was drained off for analysis. Such an amount of isobutane was supplied to the reactor to ensure a constant quantity of liquid in the system. When the system had stabilized, such an amount of cis-2-butene was added to it as to give a cis-2-butene-WHSV as given in the examples below (calculated on zeolite weight in the catalyst sample). The overall rate of flow of liquid in the system was maintained at about 4,000 g/h. The weight ratio of isobutane to cis-2-butene in the reactor supply (without considering the unreacted material fed back to the reactor) is given in the Examples below. The pressure in the reactor amounted to 21 bar.

Each time after 1 hour of reaction, the catalyst was regenerated by being washed with isobutane for 5 minutes, followed by 50 minutes of regeneration through being contacted with a solution of 1 mol % of H2 in isobutane, and then being washed with isobutane for another 5 minutes (total washing and regeneration time 1 hour). After this washing step, alkylation was started again. The process conditions during the washing steps and the regeneration step were the same as the process conditions during the reaction step.

Unless specified otherwise, the catalytic performance was measured after a steady state was reached. The performance was characterized by the olefin conversion, the research octane number (RON), the C5+ alkylate yield, and the weight percentage of undesired C9+ by-products (excl. 2,2,5-trimethylhexane), calculated on C5+ alkylate. The RON was determined as described on pages 13 and 14 of WO 9823560, the only exception being that the RON contribution of total C9+ (excl. 2,2,5-trimethylhexane) was estimated to be 84 instead of 90. The C5+ alkylate yield is defined as the weight amount of C5+ alkylate produced divided by the overall weight of olefin consumed.

EXAMPLE 1

A catalyst of the invention was tested according to the above-described test procedure. The weight ratio of isobutane to cis-2-butene in the reactor supply (without considering the unreacted material fed back to the reactor) was 20. The reaction temperature was 70° C. The cis-2-butene-WHSV was 0.21 h-1. The catalyst had the following properties:

| Catalyst composition: | |
| --- | --- |
| Solid acid: | USY-zeolite |
| Solid acid amount: | 70 wt % (based on the total weight of solid acid and matrix) |
| Hydrogenation metal: | platinum |
| Hydrogenation metal amount: | 0.34 wt % |
| Matrix: | alumina |
| Matrix amount: | 30 wt % (based on the total weight of solid acid and matrix) |
| Catalyst shape: | cylindrical extrudates |
| Pore/particle characteristics: | |
| Macropore volume: | 0.17 ml/g |
| Specific length: | 0.22 mm (average diameter: 1.0 mm, average length: 4 mm) |
| Macropore volume/ specific length | 0.77 ml/(g*mm) |
| Total pore volume: | 0.36 ml/g |

The catalytic performance is given in the Table below.

EXAMPLE 2

A catalyst with the same composition and shape as the catalyst of Example 1 was tested. The catalyst had a ratio between macropore volume and specific length of 0.64 ml/(g*mm) (macropore volume: 0.14 ml/g, specific length: 0.22 mm (average diameter: 1.0 mm, average length: 4 mm)). Its total pore volume was 0.35 ml/g. The weight ratio of isobutane to cis-2-butene in the reactor supply (without considering the unreacted material fed back to the reactor) was 19. The reaction temperature was 70° C. The cis-2-butene-WHSV was 0.21 h-1. The further test conditions were as described in Example 1. The catalytic performance is given in the Table below.

EXAMPLE 3

A catalyst with the same composition and shape as the catalyst of Example 1 was tested. It had a ratio between macropore volume and specific length of 0.41 ml/(g*mm) (macropore volume: 0.09 ml/g, specific length: 0.22 mm (average diameter: 1.0 mm, average length: 4 mm)). Its total pore volume was 0.27 ml/g. The weight ratio of isobutane to cis-2-butene in the reactor supply (without considering the unreacted material fed back to the reactor) was 19. The reaction temperature was 70° C. The cis-2-butene-WHSV was 0.21 h-1. The further test conditions were as described in Example 1. The catalytic performance is given in the Table below.

EXAMPLE 4

A catalyst with the same composition and shape as that of Example 1 was tested. It had a ratio between macropore volume and specific length of 0.49 ml/(g*mm) (macropore volume: 0.17 ml/g, specific length: 0.35 mm (average diameter: 1.7 mm, average length: 4 mm)). Its total pore volume was 0.38 ml/g. The weight ratio of isobutane to cis-2-butene in the reactor supply (without considering the unreacted material fed back to the reactor) was 26. The reaction temperature was 80° C. The cis-2-butene-WHSV was 0.19 h-1. The further test conditions were as described in Example 1. The catalytic performance is given in the Table below.

COMPARATIVE EXAMPLE A

A catalyst with the same composition and shape as the catalyst of Example 1 was tested. It had a ratio between macropore volume and specific length of 0.95 ml/(g*mm) (macropore volume: 0.21 ml/g, specific length: 0.22 mm (average diameter: 1.0 mm, average length: 4 mm)), which lies outside the claimed range. Its total pore volume was 0.50 ml/g. The weight ratio of isobutane to cis-2-butene in the reactor supply (without considering the unreacted material fed back to the reactor) was 30. The reaction temperature was 70° C. The cis-2-butene-WHSV was 0.21 h-1. The further test conditions were as described in Example 1. The catalytic performance is given in the Table below.

COMPARATIVE EXAMPLE B

A catalyst with the same composition and shape as the catalyst of Example 1 was tested. It had a ratio between macropore volume and specific length of 0.18 ml/(g*mm) (macropore volume: 0.04 ml/g, specific length: 0.22 mm (average diameter: 1.0 mm, average length: 4 mm)). Its total pore volume was 0.19 ml/g, which lies outside the claimed range. The weight ratio of isobutane to cis-2-butene in the reactor supply (without considering the unreacted material fed back to the reactor) was 27. The reaction temperature was 80° C. The cis-2-butene-WHSV was 0.19 h-1. The further test conditions were as described in Example 1. As a steady state could not be reached, the catalytic performance was measured after 60 hours. The results are given in the Table below.

Discussion:

The catalytic performance of the catalysts of the above Examples is summarized in the Table below:

|  | Ex. 1 | Ex. 2 | Ex. 3 | Ex. 4 | Com. Ex. A | Com. Ex. B |
|---|---|---|---|---|---|---|
| Total pore volume [ml/g] | 0.36 | 0.35 | 0.27 | 0.38 | 0.50 | 0.19 |
| Macropore volume/ specific length [ml/(g*mm)] | 0.77 | 0.64 | 0.41 | 0.49 | 0.95 | 0.18 |
| Olefin conversion [%] | 100 | 99.9 | 100 | 99.7 | 99.5 | 98.4 |
| wt % C9+ (excl. 2,2,5-trimethyl-hexane), calc. on C5+ alkylate | 5.3 | 6.4 | 5.0 | 6.1 | 13 | 10 |
| RON (research octane number) | 95.7 | 96.0 | 96.1 | 95.7 | 95.6 | 95.0 |
| C5+ alkylate yield [%] | 205 | 207 | 206 | 202 | 185 | 183 |

The performance of the catalysts of Comparative Examples A and B is significantly worse than that in Examples 1–4. More in particular, the C5+ alkylate yield is significantly lower than the corresponding yields of the catalysts according to the invention, whereas the weight percentage of undesired C9+ lies significantly above the corresponding values of the catalysts of Examples 1–4.

It is noted that this poor performance of the catalysts of Comparative Examples A and B is observed despite the fact that they were tested at conditions that should lead to a better catalytic performance than the conditions under which the catalysts of Examples 1–4 were tested. More in particular, the weight ratio between isobutane and cis-2-butene in Comparative Examples A and B is higher than in Examples 1–4. A higher weight ratio implies a lower amount of olefin in the reactor and thus a lower risk of excess olefin being able to react with the formed alkylate resulting in undesired C9+ products.

We claim:
1. A process for the alkylation of hydrocarbons wherein a hydrocarbon feedstock and an olefin are contacted with a catalyst at alkylation process conditions, said catalyst comprising a hydrogenation function and a solid acid, wherein the ratio between (i) the volume in catalyst pores with a diameter in the range of about 40–8000 nm and (ii) the specific length of the catalyst particles is in the range of about 0.01–0.90 ml/(g*mm) and wherein the catalyst has a total pore volume of at least about 0.20 ml/g and the volume in the catalyst pores with a diameter in the range of about 40–8000 nm is below about 0.30 ml/g.

2. The process of claim 1 wherein the hydrocarbons are saturated hydrocarbons.

3. The process of claim 1 wherein the ratio between (i) the volume in catalyst pores with a diameter in the range of about 40–8000 nm and (ii) the specific length of the catalyst particles is at least about 0.20 ml/(g*mm).

4. The process of claim 1 wherein the catalyst has a total pore volume of at least about 0.23 ml/g.

5. The process of claim 1 wherein the hydrogenation function consists essentially of a Group VIII noble metal.

6. The process of claim 1 wherein the solid acid is a Y-zeolite with a unit cell size in the range of about 24.34–24.72 angstroms.

7. The process of claim 6 wherein the solid acid is a Y zeolite with a unit cell size in the range of about 24.40–24.61 angstroms.

8. The process of claim 7 wherein the solid acid is a Y zeolite with a unit cell size in the range of about 24.45–24.58 angstroms.

9. The process of claim 1 wherein the catalyst additionally comprises a matrix material.

10. The process of claim 9 wherein the matrix material comprises alumina.

11. The process of claim 1 wherein the catalyst is free of rare earth metals and Group VIII non-noble metals.

* * * * *